US010653400B2

(12) United States Patent
Kamaraj et al.

(10) Patent No.: US 10,653,400 B2
(45) Date of Patent: May 19, 2020

(54) SPECIMEN RETRIEVAL DEVICE (71) Applicant: Covidien LP, Mansfield, MA (US)

(72) Inventors: Raja Kamaraj, Hyderabad (IN); Sabastian Koduthully George, Hyderabad (IN)

(73) Assignee: Covidien LP, Mansfield, MA (US)

( * ) Notice: Subject to any disclaimer, the term of this patent is extended or adjusted under 35 U.S.C. 154(b) by 176 days.

(21) Appl. No.: 16/012,818

(22) Filed: Jun. 20, 2018

(65) Prior Publication Data
US 2019/0038269 A1 Feb. 7, 2019

Related U.S. Application Data (60) Provisional application No. 62/541,836, filed on Aug. 7, 2017.

(51) Int. Cl.
*A61B 17/00* (2006.01)
*A61B 90/00* (2016.01)
(52) U.S. Cl.
CPC ........ *A61B 17/00234* (2013.01); *A61B 90/08* (2016.02); *A61B 2017/0046* (2013.01); *A61B 2017/00287* (2013.01); *A61B 2017/00455* (2013.01); *A61B 2017/00473* (2013.01); *A61B 2017/00477* (2013.01); *A61B 2090/0808* (2016.02)
(58) Field of Classification Search
CPC ............ A61B 17/00234; A61B 17/221; A61B 2017/2212; A61B 2017/00287
See application file for complete search history.

(56) References Cited

U.S. PATENT DOCUMENTS

| | | | |
|---|---|---|---|
| 30,471 | A | 10/1860 | Dudley |
| 35,164 | A | 5/1862 | Logan et al. |
| 156,477 | A | 11/1874 | Bradford |
| 1,609,014 | A | 11/1926 | Dowd |
| 3,800,781 | A | 4/1974 | Zalucki |
| 4,557,255 | A | 12/1985 | Goodman |
| 4,611,594 | A | 9/1986 | Grayhack et al. |
| 4,744,363 | A | 5/1988 | Hasson |

(Continued)

FOREIGN PATENT DOCUMENTS

| | | |
|---|---|---|
| DE | 3542667 A1 | 6/1986 |
| DE | 8435489 U1 | 8/1986 |

(Continued)

OTHER PUBLICATIONS

European Search Report dated Mar. 14, 2019, issued in EP 18187594.
(Continued)

*Primary Examiner* — Wade Miles
(74) *Attorney, Agent, or Firm* — Carter, DeLuca & Farrell LLP (57) ABSTRACT A specimen retrieval device includes a deployment assembly and a specimen retrieval bag supported by the deployment assembly. The deployment assembly includes an insertion tube, a shaft slidably receivable through the insertion, a handle disposed on a proximal end portion of the shaft, and a support assembly disposed on a distal end portion of the shaft. The specimen retrieval bag includes a pouch portion supported by the support assembly, a tail portion extending from the pouch portion and secured to the handle, and a closure cord extending through the pouch portion for cinching the pouch portion.

9 Claims, 8 Drawing Sheets (56) References Cited

U.S. PATENT DOCUMENTS

| | | |
|---|---|---|
| 4,790,812 A | 12/1988 | Hawkins, Jr. et al. |
| 4,852,586 A | 8/1989 | Haines |
| 4,927,427 A | 5/1990 | Kriauciunas et al. |
| 4,977,903 A | 12/1990 | Haines |
| 4,991,593 A | 2/1991 | LeVahn |
| 4,997,435 A | 3/1991 | Demeter |
| 5,037,379 A | 8/1991 | Clayman et al. |
| 5,074,867 A | 12/1991 | Wilk |
| 5,084,054 A | 1/1992 | Bencini et al. |
| 5,143,082 A | 9/1992 | Kindberg et al. |
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,201,740 A | 4/1993 | Nakao et al. |
| 5,215,521 A | 6/1993 | Cochran et al. |
| 5,224,930 A | 7/1993 | Spaeth et al. |
| 5,234,439 A | 8/1993 | Wilk et al. |
| 5,279,539 A | 1/1994 | Bohan et al. |
| 5,312,416 A | 5/1994 | Spaeth et al. |
| 5,320,627 A | 6/1994 | Sorensen et al. |
| 5,330,483 A | 7/1994 | Heaven et al. |
| 5,336,227 A | 8/1994 | Nakao et al. |
| 5,337,754 A | 8/1994 | Heaven et al. |
| 5,341,815 A | 8/1994 | Cofone et al. |
| 5,352,184 A | 10/1994 | Goldberg et al. |
| 5,354,303 A | 10/1994 | Spaeth et al. |
| 5,368,545 A | 11/1994 | Schaller et al. |
| 5,368,597 A | 11/1994 | Pagedas |
| 5,370,647 A | 12/1994 | Graber et al. |
| 5,443,472 A | 8/1995 | Li |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| 5,499,988 A | 3/1996 | Espiner et al. |
| 5,524,633 A | 6/1996 | Heaven et al. |
| 5,535,759 A | 7/1996 | Wilk |
| 5,611,803 A | 3/1997 | Heaven et al. |
| 5,618,296 A | 4/1997 | Sorensen et al. |
| 5,630,822 A | 5/1997 | Hermann et al. |
| 5,642,282 A | 6/1997 | Sonehara |
| 5,643,282 A | 7/1997 | Kieturakis |
| 5,643,283 A | 7/1997 | Younker |
| 5,645,083 A | 7/1997 | Essig et al. |
| 5,647,372 A | 7/1997 | Tovey et al. |
| 5,649,902 A | 7/1997 | Yoon |
| 5,658,296 A | 8/1997 | Bates et al. |
| 5,679,423 A | 10/1997 | Shah |
| 5,681,324 A | 10/1997 | Kammerer et al. |
| 5,720,754 A | 2/1998 | Middleman et al. |
| 5,735,289 A | 4/1998 | Pfeffer et al. |
| 5,741,271 A | 4/1998 | Nakao et al. |
| 5,755,724 A | 5/1998 | Yoon |
| 5,759,187 A | 6/1998 | Nakao et al. |
| 5,769,794 A | 6/1998 | Conlan et al. |
| 5,782,840 A | 7/1998 | Nakao |
| 5,785,677 A | 7/1998 | Auweiler |
| 5,788,709 A | 8/1998 | Riek et al. |
| 5,792,145 A | 8/1998 | Bates et al. |
| 5,814,044 A | 9/1998 | Hooven |
| 5,829,440 A | 11/1998 | Broad, Jr. |
| 5,836,953 A | 11/1998 | Yoon |
| 5,853,374 A | 12/1998 | Hart et al. |
| 5,895,392 A | 4/1999 | Riek et al. |
| 5,904,690 A | 5/1999 | Middleman et al. |
| 5,906,621 A | 5/1999 | Secrest et al. |
| 5,908,429 A | 6/1999 | Yoon |
| 5,957,884 A | 9/1999 | Hooven |
| 5,971,995 A | 10/1999 | Rousseau |
| 5,980,544 A | 11/1999 | Vaitekunas |
| 5,997,547 A | 12/1999 | Nakao et al. |
| 6,004,330 A | 12/1999 | Middleman et al. |
| 6,007,512 A | 12/1999 | Hooven |
| 6,007,546 A | 12/1999 | Snow et al. |
| 6,019,770 A | 2/2000 | Christoudias |
| 6,036,681 A | 3/2000 | Hooven |
| 6,059,793 A | 5/2000 | Pagedas |
| 6,123,701 A | 9/2000 | Nezhat |
| 6,152,932 A | 11/2000 | Ternstrom |
| 6,156,055 A | 12/2000 | Ravenscroft |
| 6,162,235 A | 12/2000 | Vaitekunas |
| 6,165,121 A | 12/2000 | Alferness |
| 6,168,603 B1 | 1/2001 | Leslie et al. |
| 6,206,889 B1 | 3/2001 | Bennardo |
| 6,228,095 B1 | 5/2001 | Dennis |
| 6,258,102 B1 | 7/2001 | Pagedas |
| 6,264,663 B1 | 7/2001 | Cano |
| 6,270,505 B1 | 8/2001 | Yoshida et al. |
| 6,277,083 B1 | 8/2001 | Eggers et al. |
| 6,280,450 B1 | 8/2001 | McGuckin, Jr. |
| 6,344,026 B1 | 2/2002 | Burbank et al. |
| 6,348,056 B1 | 2/2002 | Bates et al. |
| 6,350,266 B1 | 2/2002 | White et al. |
| 6,350,267 B1 | 2/2002 | Stefanchik |
| 6,368,328 B1 | 4/2002 | Chu et al. |
| 6,383,195 B1 | 5/2002 | Richard |
| 6,383,196 B1 | 5/2002 | Leslie et al. |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,471,659 B2 | 10/2002 | Eggers et al. |
| 6,506,166 B1 | 1/2003 | Hendler et al. |
| 6,508,773 B2 | 1/2003 | Burbank et al. |
| 6,537,273 B1 | 3/2003 | Sosiak et al. |
| 6,547,310 B2 | 4/2003 | Myers |
| 6,589,252 B2 | 7/2003 | McGuckin, Jr. |
| 6,752,811 B2 | 6/2004 | Chu et al. |
| 6,755,779 B2 | 6/2004 | Vanden Hoek et al. |
| 6,780,193 B2 | 8/2004 | Leslie et al. |
| 6,805,699 B2 | 10/2004 | Shimm |
| 6,840,948 B2 | 1/2005 | Albrecht et al. |
| 6,872,211 B2 | 3/2005 | White et al. |
| 6,887,255 B2 | 5/2005 | Shimm |
| 6,958,069 B2 | 10/2005 | Shipp et al. |
| 6,971,988 B2 | 12/2005 | Orban, III |
| 6,994,696 B2 | 2/2006 | Suga |
| 7,014,648 B2 | 3/2006 | Ambrisco et al. |
| 7,018,373 B2 | 3/2006 | Suzuki |
| 7,052,454 B2 | 5/2006 | Taylor |
| 7,052,501 B2 | 5/2006 | McGuckin, Jr. |
| 7,090,637 B2 | 8/2006 | Danitz et al. |
| 7,115,125 B2 | 10/2006 | Nakao et al. |
| 7,270,663 B2 | 9/2007 | Nakao |
| 7,273,488 B2 | 9/2007 | Nakamura et al. |
| 7,410,491 B2 | 8/2008 | Hopkins et al. |
| 7,547,310 B2 | 6/2009 | Whitfield |
| 7,618,437 B2 | 11/2009 | Nakao |
| 7,670,346 B2 | 3/2010 | Whitfield |
| 7,722,626 B2 | 5/2010 | Middleman et al. |
| 7,762,959 B2 | 7/2010 | Bilsbury |
| 7,785,251 B2 | 8/2010 | Wilk |
| 7,819,121 B2 | 10/2010 | Amer |
| 7,837,612 B2 | 11/2010 | Gill et al. |
| RE42,050 E | 1/2011 | Richard |
| 7,892,242 B2 | 2/2011 | Goldstein |
| 8,016,771 B2 | 9/2011 | Orban, III |
| 8,057,485 B2 | 11/2011 | Hollis et al. |
| 8,075,567 B2 | 12/2011 | Taylor et al. |
| 8,097,001 B2 | 1/2012 | Nakao |
| 8,152,820 B2 | 4/2012 | Mohamed et al. |
| 8,172,772 B2 | 5/2012 | Zwolinski et al. |
| 8,206,401 B2 | 6/2012 | Nakao |
| 8,337,510 B2 | 12/2012 | Rieber et al. |
| 8,343,031 B2 | 1/2013 | Gertner |
| 8,348,827 B2 | 1/2013 | Zwolinski |
| 8,388,630 B2 | 3/2013 | Teague et al. |
| 8,409,112 B2 | 4/2013 | Wynne et al. |

(56) References Cited

U.S. PATENT DOCUMENTS

| | | |
|---|---|---|
| 8,409,216 B2 | 4/2013 | Parihar et al. |
| 8,409,217 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,696,683 B2 | 4/2014 | LeVert |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,906,036 B2 | 12/2014 | Farascioni |
| 8,956,370 B2 | 2/2015 | Taylor et al. |
| 8,968,329 B2 | 3/2015 | Cabrera |
| 2002/0068943 A1 | 6/2002 | Chu et al. |
| 2002/0082516 A1 | 6/2002 | Stefanchik |
| 2003/0073970 A1 | 4/2003 | Suga |
| 2003/0100909 A1 | 5/2003 | Suzuki |
| 2003/0100919 A1 | 5/2003 | Hopkins et al. |
| 2003/0199915 A1 | 10/2003 | Shimm |
| 2003/0216773 A1 | 11/2003 | Shimm |
| 2004/0097960 A1 | 5/2004 | Terachi et al. |
| 2004/0138587 A1 | 7/2004 | Lyons |
| 2005/0085808 A1 | 4/2005 | Nakao |
| 2005/0165411 A1 | 7/2005 | Orban |
| 2005/0267492 A1 | 12/2005 | Poncet et al. |
| 2006/0030750 A1 | 2/2006 | Amer |
| 2006/0052799 A1 | 3/2006 | Middleman et al. |
| 2006/0058776 A1 | 3/2006 | Bilsbury |
| 2006/0169287 A1 | 8/2006 | Harrison et al. |
| 2006/0200169 A1 | 9/2006 | Sniffin |
| 2006/0200170 A1 | 9/2006 | Aranyi |
| 2006/0229639 A1 | 10/2006 | Whitfield |
| 2006/0229640 A1 | 10/2006 | Whitfield |
| 2007/0016224 A1 | 1/2007 | Nakao |
| 2007/0016225 A1 | 1/2007 | Nakao |
| 2007/0073251 A1 | 3/2007 | Zhou et al. |
| 2007/0088370 A1 | 4/2007 | Kahle et al. |
| 2007/0135780 A1 | 6/2007 | Pagedas |
| 2007/0135781 A1 | 6/2007 | Hart |
| 2007/0186935 A1 | 8/2007 | Wang et al. |
| 2008/0188766 A1 | 8/2008 | Gertner |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2008/0300621 A1 | 12/2008 | Hopkins et al. |
| 2008/0312496 A1 | 12/2008 | Zwolinski |
| 2009/0043315 A1 | 2/2009 | Moon |
| 2009/0082779 A1 | 3/2009 | Nakao |
| 2009/0182292 A1 | 7/2009 | Egle et al. |
| 2009/0192510 A1 | 7/2009 | Bahney |
| 2009/0240238 A1 | 9/2009 | Grodrian et al. |
| 2010/0000471 A1 | 1/2010 | Hibbard |
| 2010/0152746 A1 | 6/2010 | Ceniccola et al. |
| 2011/0087235 A1 | 4/2011 | Taylor et al. |
| 2011/0184311 A1 | 7/2011 | Parihar et al. |
| 2011/0184434 A1 | 7/2011 | Parihar et al. |
| 2011/0184435 A1 | 7/2011 | Parihar et al. |
| 2011/0184436 A1 | 7/2011 | Shelton, IV et al. |
| 2011/0190779 A1 | 8/2011 | Gell et al. |
| 2011/0190781 A1 | 8/2011 | Collier et al. |
| 2011/0190782 A1 | 8/2011 | Fleming et al. |
| 2011/0264091 A1 | 10/2011 | Koppleman et al. |
| 2011/0299799 A1 | 12/2011 | Towe |
| 2012/0046667 A1 | 2/2012 | Cherry et al. |
| 2012/0083795 A1 | 4/2012 | Fleming et al. |
| 2012/0083796 A1 | 4/2012 | Grover et al. |
| 2012/0203241 A1 | 8/2012 | Williamson, IV |
| 2013/0023895 A1 | 1/2013 | Saleh |
| 2013/0103042 A1 | 4/2013 | Davis |
| 2013/0116592 A1 | 5/2013 | Whitfield |
| 2013/0190773 A1 | 7/2013 | Carlson |
| 2013/0218170 A1 | 8/2013 | Uznanski et al. |
| 2013/0245636 A1 | 9/2013 | Jansen |
| 2013/0274758 A1 | 10/2013 | Young et al. |
| 2013/0325025 A1 | 12/2013 | Hathaway et al. |
| 2014/0046337 A1 | 2/2014 | O'Prey et al. |
| 2014/0058403 A1 | 2/2014 | Menn et al. |
| 2014/0180303 A1 | 6/2014 | Duncan et al. |
| 2014/0222016 A1 | 8/2014 | Grover et al. |
| 2014/0236110 A1 | 8/2014 | Taylor et al. |
| 2014/0243865 A1 | 8/2014 | Swayze et al. |
| 2014/0249541 A1 | 9/2014 | Kahle et al. |
| 2014/0276913 A1 | 9/2014 | Tah et al. |
| 2014/0303640 A1 | 10/2014 | Davis et al. |
| 2014/0309656 A1 | 10/2014 | Gal et al. |
| 2014/0330285 A1 | 11/2014 | Rosenblatt et al. |
| 2014/0350567 A1 | 11/2014 | Schmitz et al. |
| 2014/0371759 A1 | 12/2014 | Hartoumbekis |
| 2014/0371760 A1 | 12/2014 | Menn |
| 2015/0018837 A1 | 1/2015 | Sartor et al. |
| 2015/0045808 A1 | 2/2015 | Farascioni |

FOREIGN PATENT DOCUMENTS

| | | |
|---|---|---|
| DE | 4204210 A1 | 8/1992 |
| DE | 19624826 A1 | 1/1998 |
| EP | 0947166 A2 | 10/1999 |
| EP | 1685802 A1 | 8/2006 |
| EP | 1707126 A1 | 10/2006 |
| EP | 2005900 A2 | 12/2008 |
| EP | 2184014 A2 | 5/2010 |
| EP | 2436313 A2 | 4/2012 |
| EP | 2474270 A2 | 7/2012 |
| FR | 1272412 A | 9/1961 |
| GB | 246009 A | 1/1926 |
| WO | 9315675 A1 | 8/1993 |
| WO | 9509666 A1 | 4/1995 |
| WO | 0135831 A1 | 5/2001 |
| WO | 2004002334 A1 | 1/2004 |
| WO | 2004112571 A2 | 12/2004 |
| WO | 2005112783 A1 | 12/2005 |
| WO | 2006110733 | 10/2006 |
| WO | 2007048078 A1 | 4/2007 |
| WO | 2007048085 A2 | 4/2007 |
| WO | 2008114234 A2 | 9/2008 |
| WO | 2009149146 A1 | 12/2009 |
| WO | 2011090862 A2 | 7/2011 |
| WO | 2014134285 A1 | 9/2014 |

OTHER PUBLICATIONS

European Search Report EP 12191639.9 dated Feb. 20, 2013.
European Search Report EP 11250837.9 dated Sep. 10, 2013.
European Search Report EP 11250838.7 dated Sep. 10, 2013.
European Search Report EP 13170118.7 dated Dec. 5, 2013.
European Search Report EP 12165852 dated Jun. 20, 2012.
http://www.biomaterials.org/week/bio17.cfm, definition and examples of hydrogels.
European Search Report EP 12150271 dated Jan. 14, 2013.
European Search Report EP 12193450 dated Feb. 27, 2013.
European Search Report EP 12189517.1 dated Mar. 6, 2013.
European Search Report EP 12158873 dated Jul. 19, 2012.
European Search Report EP 11250836 dated Sep. 12, 2013.

SPECIMEN RETRIEVAL DEVICE

CROSS-REFERENCE TO RELATED APPLICATIONS

This application claims the benefit of and priority to U.S. Provisional Patent Application No. 62/541,836 filed Aug. 7, 2017, the entire disclosure of which is incorporated by reference herein.

BACKGROUND

Technical Field

The present disclosure relates to specimen retrieval devices. More particularly, the present disclosure relates to an apparatus and method for releasably securing a specimen retrieval bag to a deployment device of a specimen retrieval device.

Background of Related Art

Surgical devices for the endoscopic retrieval of specimens, e.g., appendix, ectopic pregnancy, gallbladder, gallstones, lymph nodes, ovaries, small sections of bowel, and other tissue structures, are known, and typically include a specimen retrieval bag and a deployment device for deploying the specimen retrieval bag. Deployment devices generally include an insertion tube, and a deployment shaft extending through the insertion tube. The specimen retrieval bag is releasably secured to a deployment handle on the proximal end of the deployment shaft and includes a closure string or cord for cinching a pouch of the specimen retrieval bag. The closure string of some specimen retrieval bags are attached to a ring, with the ring being attached to the deployment handle. See, for example, U.S. Pat. No. 5,647,372 ("the '372 patent"), the content of which is incorporated herein by reference in its entirety. Alternatively, the closure string may be wrapped around the deployment handle, or extend unattached from the distal end of the insertion tube.

In each of these configurations, the clinician may accidently and/or prematurely pull the closure cord, thereby prematurely clinching the specimen retrieval bag and/or separating the specimen retrieval bag from the deployment device. Therefore, it would be beneficial to have a specimen retrieval device having a deployment assembly that includes a feature for selectively securing the specimen retrieval bag to a handle of the deployment device.

SUMMARY

Accordingly, a specimen retrieval device is provided. The specimen retrieval device includes a deployment assembly and a specimen retrieval bag supported by the deployment assembly. The deployment assembly includes an insertion tube, a shaft slidably receivable through the insertion tube and defining a longitudinal axis, a handle disposed on a proximal end portion of the shaft, and a support assembly disposed on a distal end portion of the shaft. The specimen retrieval bag includes a pouch portion supported by the support assembly, a tail portion extending from the pouch portion and secured to the handle, and a closure cord extending through the pouch portion for cinching the pouch portion.

In embodiments, the handle of the deployment assembly includes a post for engaging the tail portion of the specimen retrieval bag. The post may include a mushroom-shape. The post may include an atraumatic free end. The post may define a notch for receiving a portion of the tail portion of the specimen retrieval bag. The tail portion of the specimen retrieval bag may define an opening configured to be received about the post. A force required to separate the tail portion of the specimen retrieval bag from the post may be approximately 2-lbf. The handle may define a cutout with the post disposed within the cutout.

In embodiments, the specimen retrieval bag is secured to the deployment assembly until the tail portion of the specimen retrieval bag is separated from the handle.

A deployment assembly is also provided. The deployment assembly includes an insertion tube, a shaft slidably receivable through the insertion tube and defining a longitudinal axis, a handle disposed on a proximal end portion of the shaft, the handle including a post for securing a tail portion of a specimen retrieval bag, and a support assembly disposed on a distal end portion of the shaft.

In embodiments, the handle of the deployment assembly includes a post for engaging a tail portion of a specimen retrieval bag. The post may include a mushroom-shape. The post may include an atraumatic free end. The post may define a notch for receiving a portion of a tail portion of a specimen retrieval bag. A force required to separate a tail portion of a specimen retrieval bag from the post may be approximately 2-lbf. The handle may define a cutout with the post disposed within the cutout.

BRIEF DESCRIPTION OF THE DRAWINGS

The accompanying drawings, which are incorporated in and constitute a part of this specification, illustrate embodiments of the specimen retrieval device and, together with a general description given above, and the detailed description of the embodiment(s) given below, serve to explain the principles of the disclosure, wherein.

DETAILED DESCRIPTION

Embodiments of the presently disclosed specimen retrieval device will now be described in detail with reference to the drawings in which like reference numerals designate identical or corresponding elements in each of the several views. As is common in the art, the term "proximal" refers to that part or component closer to the clinician or operator, e.g., surgeon or clinician, while the term "distal" refers to that part or component further away from the clinician.

Figure 1:
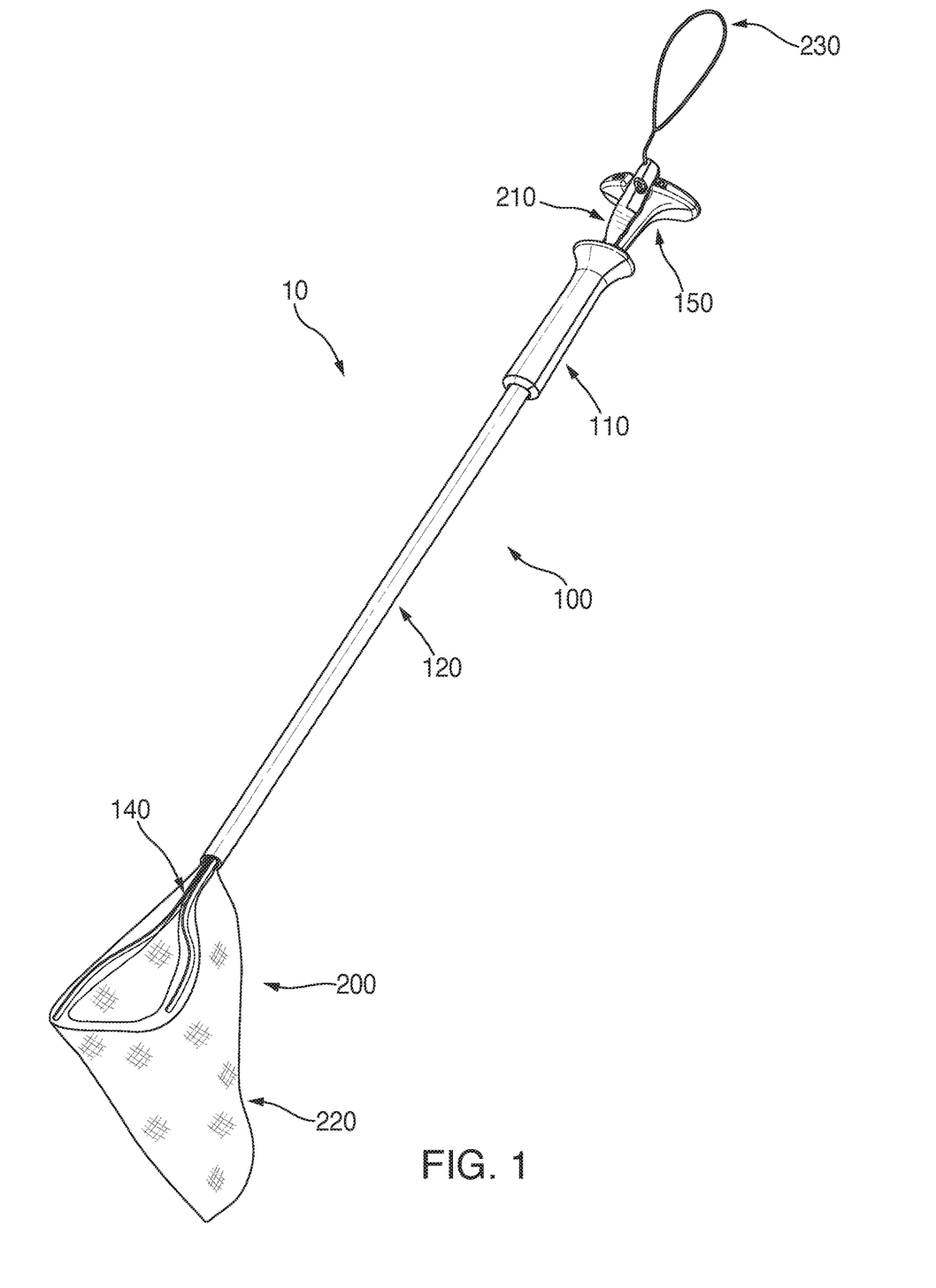
FIG. 1 is a perspective view of a specimen retrieval device according to an embodiment of the present disclosure, in an extended or deployed condition.

With reference initially to FIG. 1, a specimen retrieval device according to an embodiment of the present disclosure is shown generally as specimen retrieval device 10. The specimen retrieval device 10 includes a deployment assembly 100, and a specimen retrieval bag 200 releasably secured to the deployment assembly 100. As will be described in detail below, the deployment assembly 100 is configured such that a tail portion 210 of the specimen retrieval bag 200 is secured to a deployment handle 150 of the deployment assembly 100 to prevent premature cinching and/or separation of the specimen retrieval bag from the deployment assembly 100.

Figure 2:
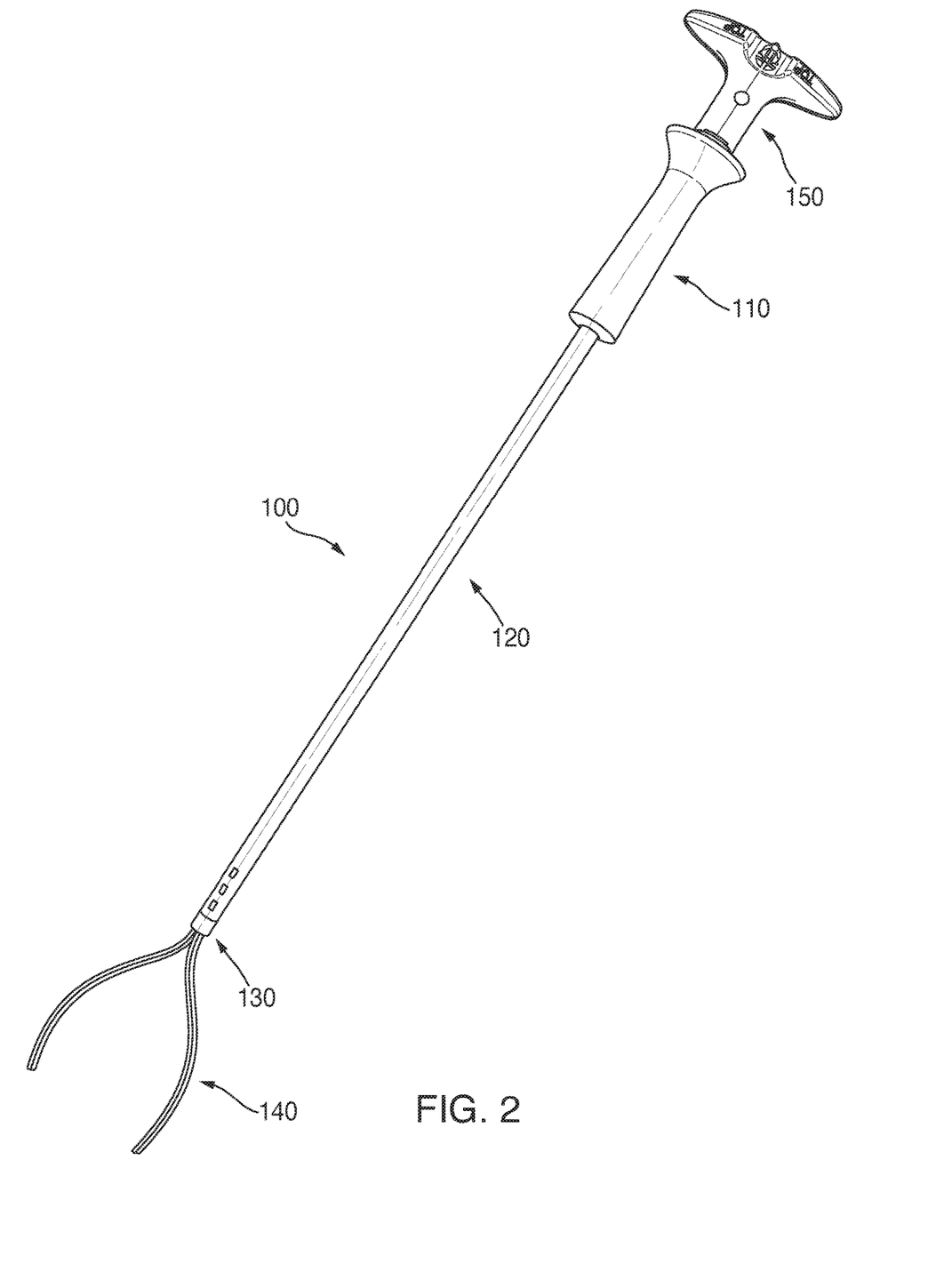
FIG. 2 is a perspective view of a deployment assembly of the specimen retrieval device shown in FIG. 1.
Figure 3:
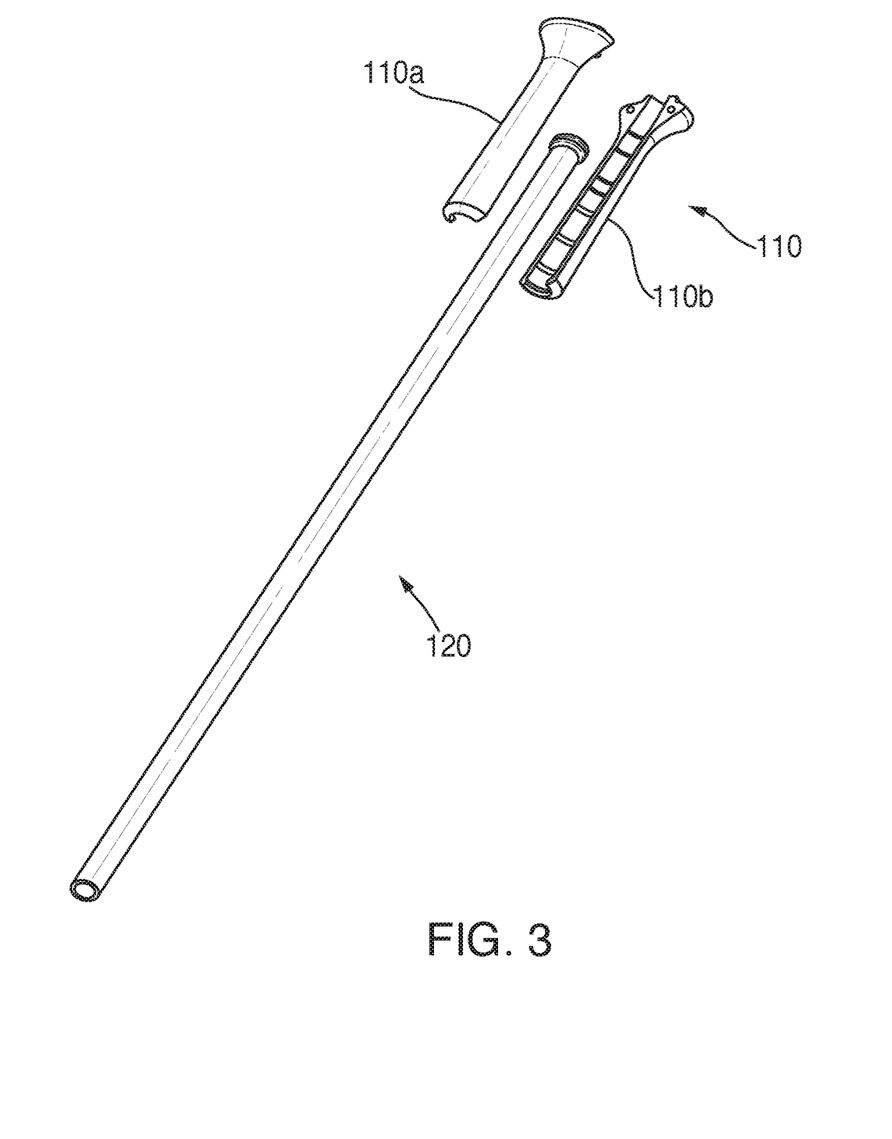
FIG. 3 is a perspective view, with parts separated, of a handle assembly and an insertion tube of the deployment assembly shown in FIG. 2.

Turning to FIGS. 2 and 3, the deployment assembly 100 of the specimen retrieval device 10 (FIG. 1) includes a handle assembly 110, and an insertion tube or sleeve 120 secured to, and extending distally from, the handle assembly 110. As shown, the handle assembly 110 is a tubular body formed of first and second half sections 110a, 110b. The handle assembly 110 may include any suitable structure, and may be knurled (not shown), coated with a slip resistant material (not shown), and/or otherwise configured to facilitate operable engagement by a clinician.

With continued reference to FIGS. 2 and 3, the insertion tube 120 of the deployment assembly 100 is configured for receipt in a patient either directly through an incision, or with the assistance of an access port, trocar, or other access device (not shown). In embodiments, the insertion tube 120 of the deployment assembly 100 is configured to be received through a 10 mm and/or a 12 mm access device (not shown). A sleeve (not shown) may be received about the insertion tube 120 to accommodate use of the specimen retrieval device 10 through access devices having openings of a larger size.

Figure 4:
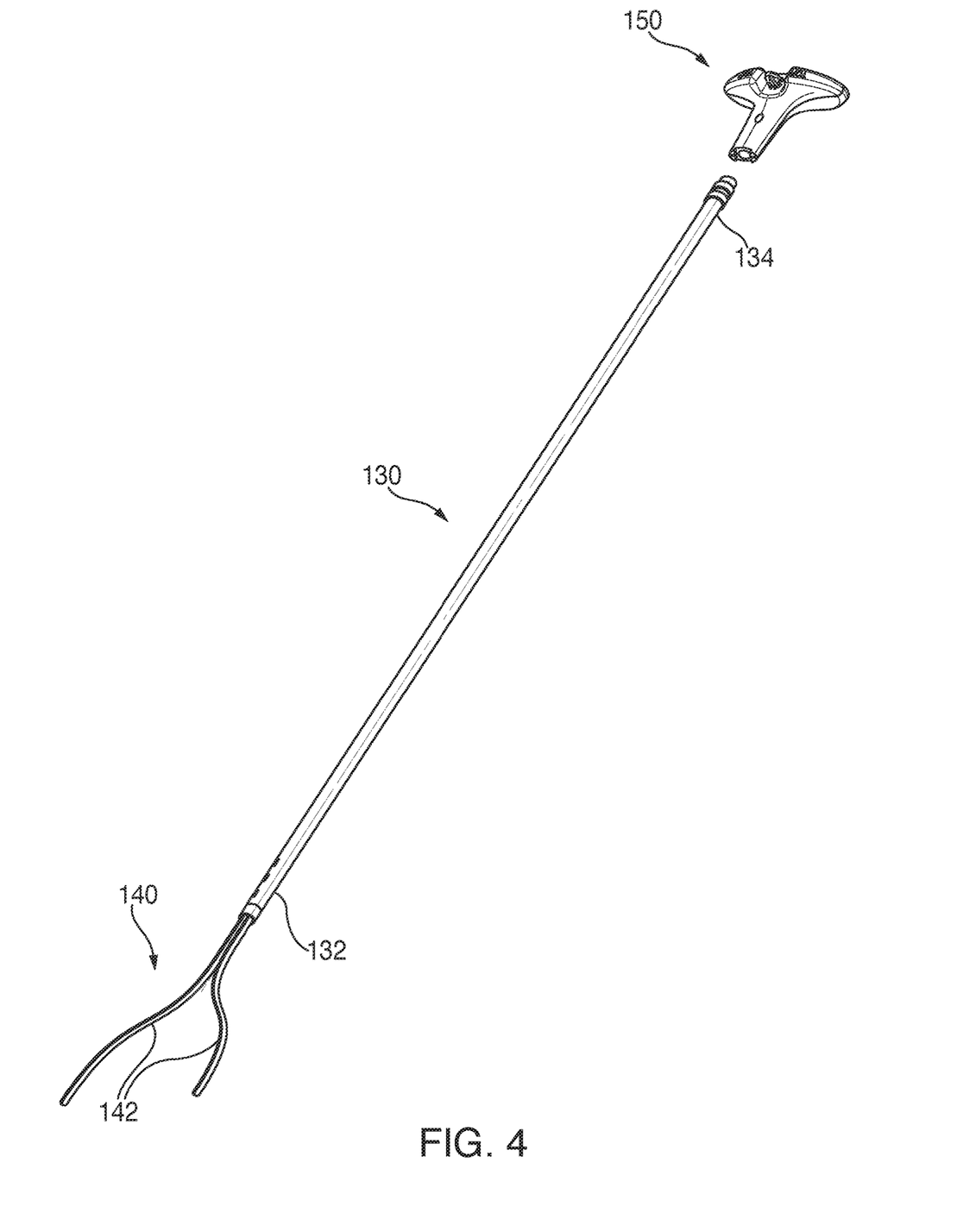
FIG. 4 is a perspective view of a deployment shaft, a support assembly, and a deployment handle of the deployment assembly shown in FIG. 2.

With additional reference to FIG. 4, the deployment assembly 100 of the specimen retrieval device 10 further includes a deployment shaft 130 having a support assembly 140 supported on a distal portion 132 of the deployment shaft 130, and a deployment handle 150 disposed on a proximal portion 134 of the deployment shaft 130. The deployment shaft 130 and the support assembly 140 are configured to be slidably received within the insertion tube 120 (FIG. 2) of the deployment assembly 100.

The support assembly 140 of the deployment assembly 100 includes a flexible fork 142 for releasably supporting a specimen retrieval bag 200. The flexible fork 142 is configured to maintain the pouch portion 220 of the specimen retrieval bag 200 in an open position when the deployment assembly 100 is in an advanced or deployed position (FIG. 1). The open fork configuration of the flexible fork 142 of the deployment assembly 100, as opposed to a loop, for supporting the specimen retrieval bag 200 allows for a larger opening for the specimen retrieval bag 200.

Figure 5:
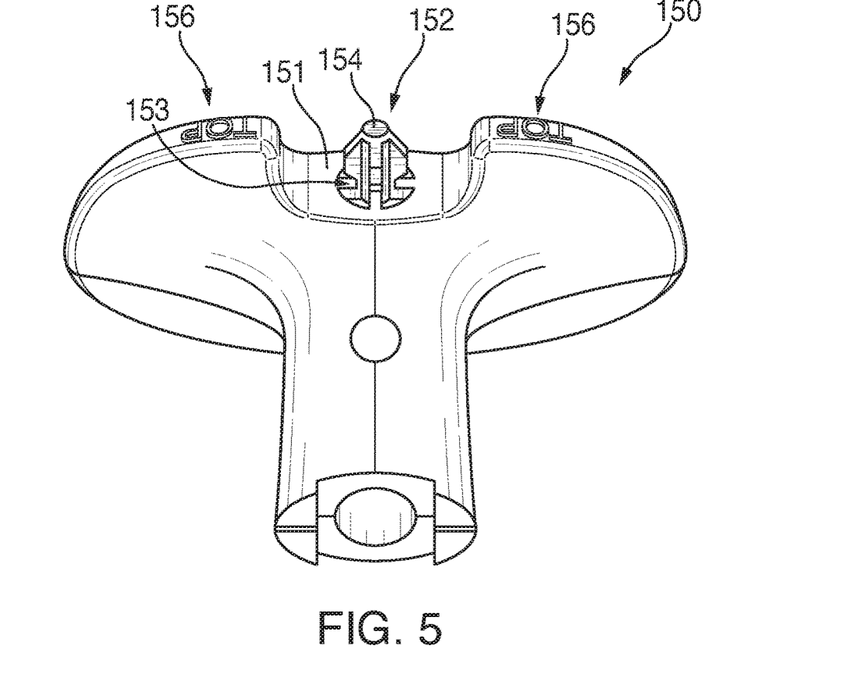
FIG. 5 is an enlarged perspective view of the deployment handle shown in FIG. 4.
Figure 6:
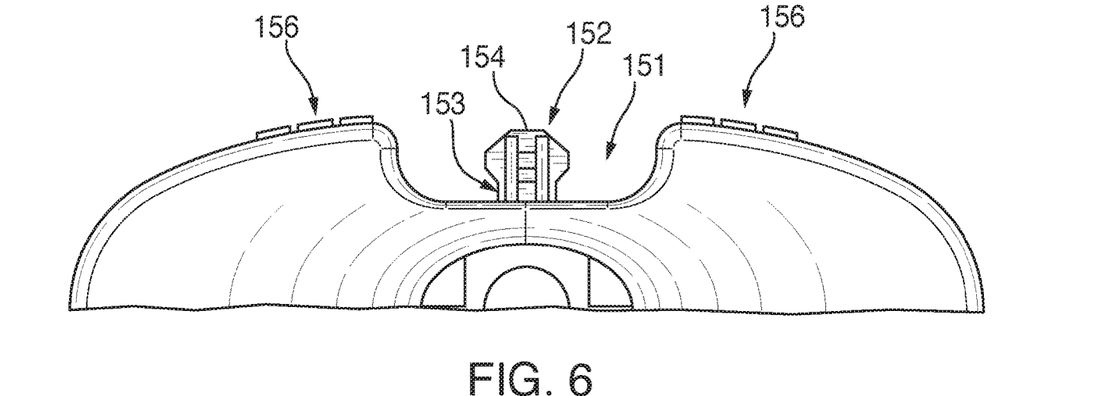
FIG. 6 is an end sectional view of the handle assembly shown in FIGS. 4 and 5.

With continued reference to FIG. 4, and additional reference to FIGS. 5 and 6, the deployment handle 150 of the deployment assembly 100 is configured to facilitate engagement by a clinician. More particularly, the deployment handle 150 of the deployment assembly 100 is configured to facilitate retraction and advancement of the deployment shaft 140 relative to the handle assembly 110, as indicated by arrows "A" and "B", respectively, shown in FIG. 8. As shown, the deployment handle 150 includes a substantially T-shaped body, although other suitable configurations are envisioned, e.g., looped handle.

Figure 7:
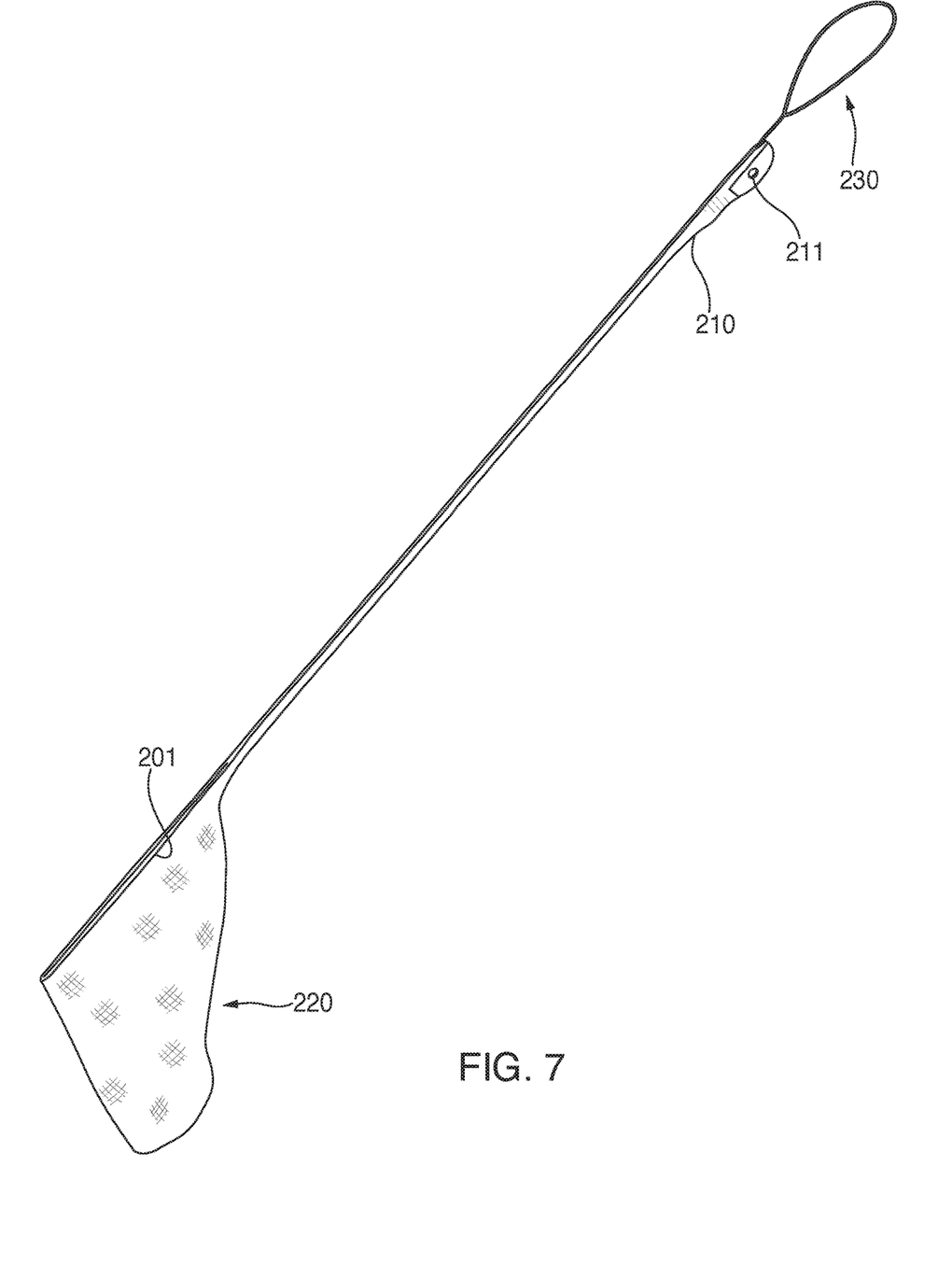
FIG. 7 is a perspective view of a specimen retrieval bag of the specimen retrieval device shown in FIG. 1.

With reference still to FIGS. 5 and 6, the deployment handle 150 of the deployment assembly 100 defines a notch or cutout 151 for receiving a tail portion 210 (FIG. 7) of the specimen retrieval bag 200 (FIG. 7). A post 152 is disposed within the notch 151 of the deployment handle 150, and is configured to engage the tail portion 210 of the specimen retrieval bag 200. The post 152 includes a rounded or atraumatic free end 154 to permit receipt of the tail portion 210 of the specimen retrieval bag 200 about the post 152 without damaging the specimen retrieval bag 200. The post 152 defines a notch 153 for securely receiving the tail portion 210 of the specimen retrieval bag 200 and maintaining the tail portion 210 about the post 152. As seen in FIG. 6, the post 152 of the deployment handle 150 includes a substantially mushroom-shaped body, although it is envisioned that the post 152 may include any suitable shape.

In embodiments, the force required to separate the tail portion 210 of the specimen retrieval bag 200 from the post 152 of the deployment handle 150 of the deployment assembly 100 is 2 pound-force (lbf). It is envisioned that the separation force may be greater or less than 2-lbf.

With particular reference to FIG. 5, the deployment handle 150 of the deployment assembly 100 includes indicia 156 for facilitating orientation of the deployment handle 150 during deployment. More particularly, and as shown, the indicia 156 reads, "TOP", to indicate to the clinician that the deployment handle 150 should be oriented with the indicia 156 facing upwards or towards the clinician. It is envisioned that the deployment handle 150 may include other indicia, or be absent of indicia.

With reference now to FIG. 7, the specimen retrieval bag 200 of the specimen retrieval device 10 (FIG. 1) is configured to be supported and deployed by the deployment assembly 100 (FIG. 2). The specimen retrieval bag 200 includes the tail portion 210, and a pouch portion 220 from which the tail portion 210 extends. The pouch portion 220 of the specimen retrieval bag 200 the may be formed, at least partially of, rip stop nylon or other suitable material. The tail portion 210 and the pouch portion 220 of the specimen retrieval bag 200 may be constructed of the same or different material. In embodiments, the tail portion 210 and the pouch portion 220 are integrally formed. Alternatively, the tail portion 210 and the pouch portion 220 may be secured together in any suitable fashion, e.g., welding, sewing, adhesive.

Figure 9:
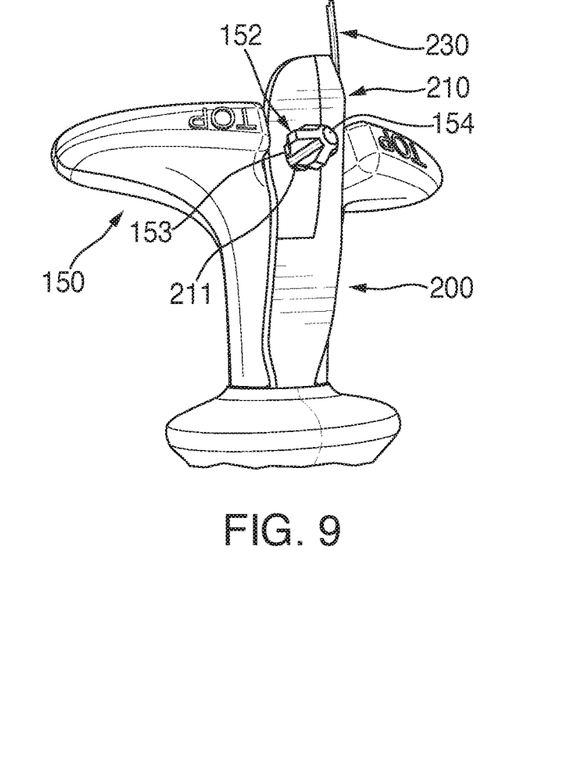
FIG. 9 is a perspective view of the deployment handle shown in FIGS. 4-6 and a tail portion of the specimen retrieval bag shown in FIG. 7, with the tail portion secured to the deployment handle.

As noted above, the tail portion 210 of the specimen retrieval bag 200 is configured to engage the deployment handle 150 of the deployment assembly 100 to releasably secure the specimen retrieval bag 200 to the deployment assembly 100. More particularly, the tail portion 210 of the specimen retrieval bag 200 defines an opening 211 configured to receive the post 152 of the deployment handle 150 of the deployment assembly 100 (FIG. 9). The tail portion 210 of the specimen bag 200 may be reinforced about the opening 211 to prevent tearing of the tail portion 210 as the tail portion 210 is received about the post 152 of the deployment handle 150 and when the tail portion 210 is separated from the deployment handle 150.

The pouch portion 220 of the specimen retrieval bag 200 includes passages (not shown) for receiving the flexible fork 142 (FIG. 4) of the support assembly 140 (FIG. 4) disposed on the distal end 132 (FIG. 4) of the deployment shaft 130 (FIG. 4). When the flexible fork 142 of the deployment assembly 100 is received within the openings in the pouch portion 220 of the specimen retrieval bag 200 and the tail portion 210 of the specimen retrieval bag 200 is secured to the post 152 of the deployment handle 150, the specimen retrieval bag 200 is secured to the deployment assembly 100. In this manner, the clinician cannot accidentally and/or prematurely cinch the specimen retrieval bag 200 and/or separate the specimen retrieval bag from the deployment assembly 100.

The specimen retrieval bag 200 of the specimen retrieval device 10 (FIG. 1) may be configured, as shown, with a substantial triangular configuration, or may instead have alternative configurations, e.g., cylindrical. In embodiments, the specimen retrieval bag 200 may be configured for use with a morcellator. The specimen retrieval bag 200 may include a pouch portion 220 having a volume of any size. In embodiments the volume of the pouch portion 220 is between 275 ml-1200 ml.

A closure cord 230 extends the length of the specimen retrieval bag 200 within a longitudinal passage 201 of the specimen retrieval bag 200. Following receipt of tissue within the pouch portion 220 and withdrawal of the support assembly 140 (FIG. 4) from within the pouch portion 220, the closure cord 230 operates to cinch the pouch portion 220 of the specimen retrieval bag 200, by pulling closure cord 230 proximally relative to the pouch portion 220 and/or deployment shaft 130. Once closed, the pouch portion 220 may be opened manually with graspers or other suitable instrument in the event access to the pouch portion 220 is necessary, e.g., to remove air from within the pouch portion 220 when removing the specimen retrieval bag 200 from a body cavity of a patient. For a detailed description of an exemplary closure cord, please refer to the '372 patent, the content of which was previously incorporated by reference.

The specimen retrieval device 10 may be provided to a clinician, as shown in FIG. 1, with the specimen retrieval bag 200 secured to the deployment assembly 100, and the deployment assembly 100 in the advance or deployed condition. Alternatively, the clinician may be required to secure the specimen retrieval bag 200 to the deployment assembly 100. It is envisioned that the specimen retrieval device 10 may be provided to the clinician as a kit including the deployment assembly 100 and one or more specimen retrieval bags 200, of the same or different configurations.

Figure 8:
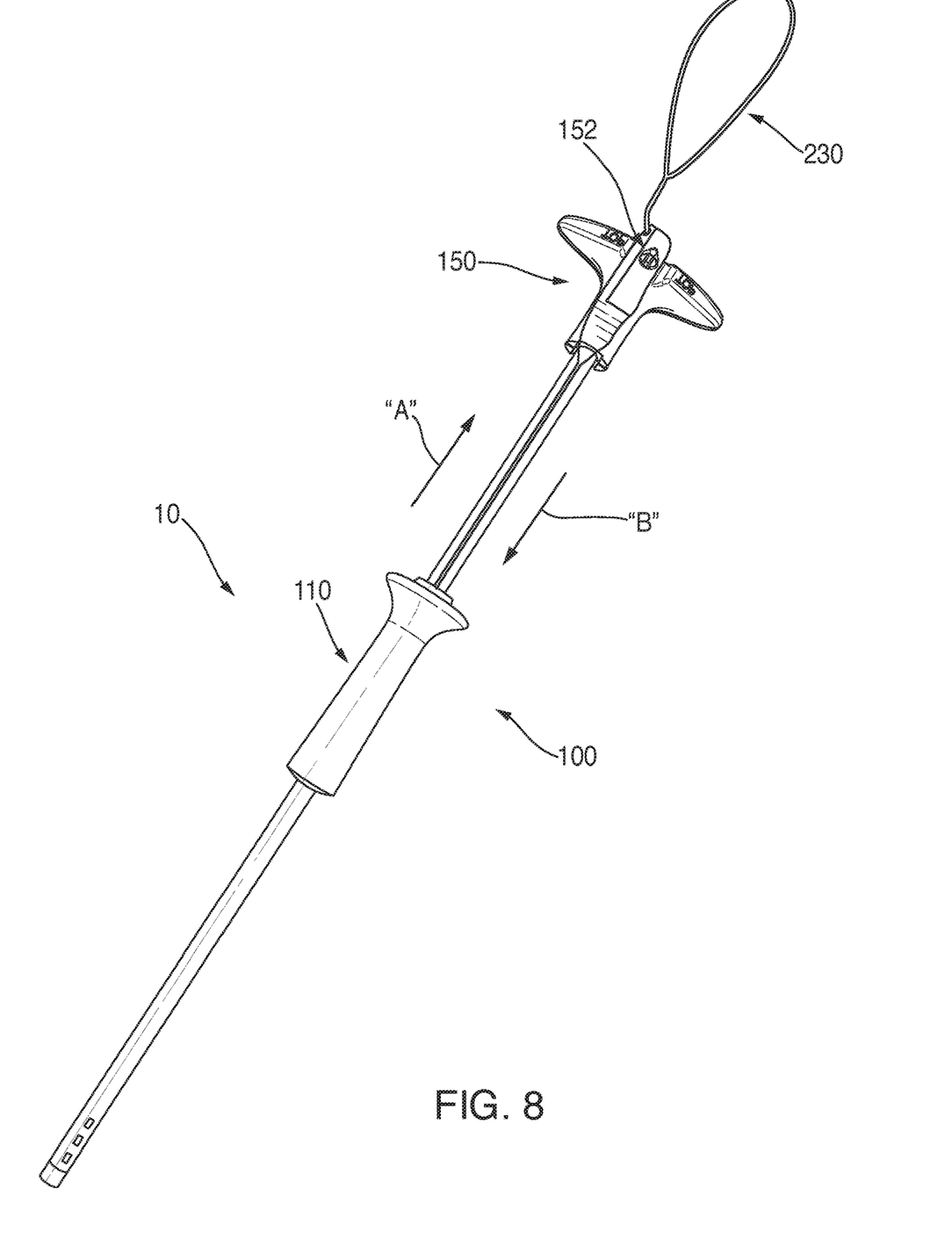
FIG. 8 is a perspective view of the specimen retrieval device shown in FIG. 1, in a retracted or collapsed condition.

After the specimen retrieval bag 200 is secured to the deployment assembly 100, initial operation of the deployment assembly 100 requires retraction of the deployment handle 150 relative to the handle assembly 110, as indicated by arrow "A" in FIG. 8, to cause the pouch portion 220 of the specimen retrieval bag 200 to be received within the insertion tube 120 of the deployment assembly 100.

Once the pouch portion 220 of the specimen retrieval bag 200 is received within the insertion tube 120 of the deployment assembly 100, the insertion tube 120 is inserted into a patient through an incision, with or without the aid of an access device, e.g., trocar, access port. The deployment handle 150 of the deployment assembly 100 may then be advanced relative to the handle assembly 110, as indicated by arrow "B" in FIG. 8, to deploy the pouch portion 220 of the specimen retrieval bag 200. As noted above, the flexible fork 142 forming the support assembly 140 for the specimen retrieval bag 200 opens the pouch portion 220 of the specimen retrieval bag 200 to permit receipt of tissue within the pouch portion 220.

Figure 10:
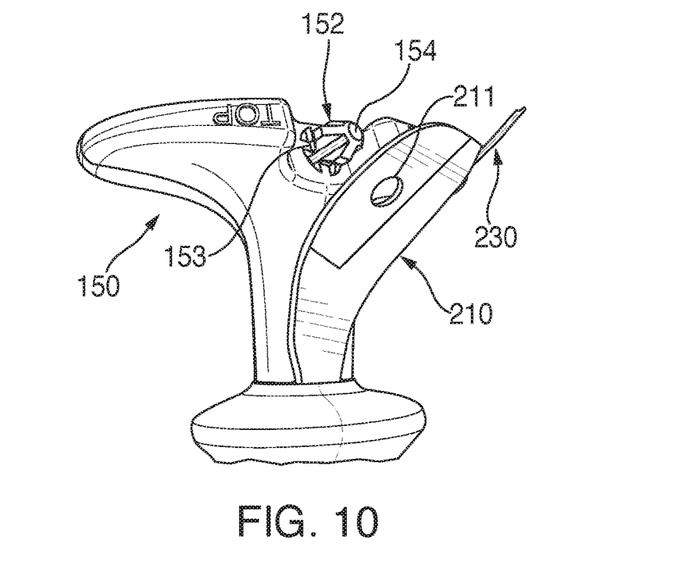
FIG. 10 is a perspective view of the deployment handle and the tail portion of the specimen retrieval bag shown in FIG. 9, with the tail portion separated from the deployment handle.

Removal of the specimen retrieval bag 200 of the specimen retrieval device 10 following a placement of tissue within the pouch portion 220 of the specimen retrieval bag 200 is a multi-step process. With reference to FIG. 10, initially, the tail portion 210 of the specimen retrieval bag 200 is separated from the post 152 of the deployment handle 152 of the deployment assembly 100. As noted above, in embodiments, the separation force is approximately 2-lbf. Once the tail portion 210 of the specimen retrieval bag 200 is separated from the deployment handle 150, the flexible fork 142 of the support assembly 140 may be retracted from within the pouch portion 220 of the specimen retrieval bag 200 by retracting the deployment handle 150 relative to the handle assembly 110 to withdraw the deployment shaft 130 and support assembly 140 completely from the insertion tube 120.

Once the deployment handle 150 and attached deployment shaft 130 and support assembly 140 of the deployment assembly 100 are withdrawn from the insertion tube 110 of the deployment assembly 100, the closure cord 230 of the specimen retrieval bag 200 is pulled relative to the tail portion 210 to cause the closure of the pouch portion 220 of the specimen retrieval bag 200. As noted above, the pouch portion 220 of the specimen retrieval bag 200 may be reopened at any time using graspers or other suitable device (not shown).

After cinching the pouch portion 220 of the specimen retrieval bag 200, the insertion tube 120 of the deployment assembly 100 is removed from about the tail portion 210 of the specimen retrieval bag 200. The tail portion 210 of the specimen retrieval bag 200 and/or the closure cord 230 is then used to retract the specimen retrieval bag 200, with captured tissue, through the incision (not shown) in the patient (not shown). Any air captured in the pouch portion 220 of the specimen retrieval bag 200 may be released by reopening the pouch portion 220. The pouch portion 220 of the specimen retrieval bag 200 may then be reclosed by pulling on the closure cord 230 relative to the tail portion 210 of the specimen retrieval bag 200.

It is envisioned that the deployment assembly 100 may be used more than once during a surgical procedure. It is further envisioned that the deployment assembly 100 may be sterilized and reused.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A specimen retrieval device comprising:
    a deployment assembly including,
        an insertion tube;
        a shaft slidably receivable through the insertion tube;
        a handle disposed on a proximal end portion of the shaft; and
        a support assembly disposed on a distal end portion of the shaft; and
    a specimen retrieval bag supported by the deployment assembly, the specimen retrieval bag including,
        a pouch including a pouch portion supported by the support assembly and a tail portion extending from the pouch portion to the handle and secured to the handle; and a closure cord extending through the pouch portion for cinching the pouch portion.

2. The specimen retrieval device of claim 1, wherein the handle of the deployment assembly includes a post for engaging the tail portion of the specimen retrieval bag.

3. The specimen retrieval device of claim 2, wherein the post includes a mushroom-shape.

4. The specimen retrieval device of claim 2, wherein the post includes an atraumatic free end.

5. The specimen retrieval device of claim 2, wherein the post defines a notch for receiving a portion of the tail portion of the specimen retrieval bag.

6. The specimen retrieval device of claim 2, wherein the tail portion of the specimen retrieval bag defines an opening configured to be received about the post.

7. The specimen retrieval device of claim 6, wherein a force required to separate the tail portion of the specimen retrieval bag from the post is approximately 2-lbf.

8. The specimen retrieval device of claim 2, wherein the handle defines a cutout and the post is disposed within the cutout.

9. The specimen retrieval device of claim 1, wherein the specimen retrieval bag is secured to the deployment assembly until the tail portion of the specimen retrieval bag is separated from the handle.

* * * * *